United States Patent
Tran et al.

(10) Patent No.: US 10,262,107 B1
(45) Date of Patent: Apr. 16, 2019

(54) PHARMACOGENETIC DRUG INTERACTION MANAGEMENT SYSTEM

(71) Applicant: Bao Tran, Saratoga, CA (US)

(72) Inventors: Bao Tran, Saratoga, CA (US); Ha Tran, Saratoga, CA (US)

(*) Notice: Subject to any disclaimer, the term of this patent is extended or adjusted under 35 U.S.C. 154(b) by 0 days.

(21) Appl. No.: 15/090,466

(22) Filed: Apr. 4, 2016

Related U.S. Application Data

(63) Continuation-in-part of application No. 13/843,903, filed on Mar. 15, 2013, now abandoned.

(51) Int. Cl.
*G06F 19/00* (2018.01)
*G06N 20/00* (2019.01)

(52) U.S. Cl.
CPC ........... *G06F 19/326* (2013.01); *G06N 20/00* (2019.01)

(58) Field of Classification Search
CPC .. A61K 31/00; A61K 45/06; C12Q 2563/131; C12Q 2563/179; C12Q 1/6804; G01N 1/28; G01N 33/5047; G01N 33/6893; G01N 35/1095
USPC .......................................................... 705/2
See application file for complete search history.

(56) References Cited

U.S. PATENT DOCUMENTS

| | | | | |
|---|---|---|---|---|
| 2004/0038927 | A1* | 2/2004 | Borsook | A61K 31/7076 514/46 |
| 2005/0208512 | A1* | 9/2005 | Sadee | C12Q 1/6886 435/6.13 |
| 2006/0099704 | A1* | 5/2006 | Predki | G01N 33/6842 705/301 |
| 2007/0248955 | A1* | 10/2007 | McCullough | C12Q 1/6827 435/6.16 |
| 2008/0051937 | A1* | 2/2008 | Khan | B65B 3/003 700/240 |
| 2009/0167531 | A1* | 7/2009 | Ferguson | G06F 19/3462 340/572.1 |
| 2010/0073202 | A1* | 3/2010 | Mazed | G06F 1/1613 340/999 |
| 2011/0178359 | A1* | 7/2011 | Hirschman | G16H 20/17 600/4 |
| 2013/0028480 | A1* | 1/2013 | Rothschild | G06F 19/3456 382/103 |
| 2014/0206015 | A1* | 7/2014 | Micallef | G01N 33/5308 435/6.19 |
| 2014/0303989 | A1* | 10/2014 | Ferguson | G06F 21/6245 705/2 |
| 2014/0358937 | A1* | 12/2014 | Thomas | G06F 17/3033 707/747 |

* cited by examiner

*Primary Examiner* — Reginald R Reyes
(74) *Attorney, Agent, or Firm* — Tran & Associates

(57) ABSTRACT

A system includes a substance to be consumed by a subject and one or more indicia labeling the substance with: genomic biomarkers; drug exposure and clinical response variability; risk for adverse events; genotype-specific dosing; polymorphic drug target and disposition genes; and treatment based on the biomarker.

20 Claims, 8 Drawing Sheets

| |
|---|
| 10 – perform reading of substance content from RF tag or barcode on a secure bottle |
| 20 – cryptographically identify content for the substance |
| 30 - identified substance can be added to an interaction list |
| 40 - if additional substances remain to be scanned (RF/Bar Code), loop back to 10 |
| 50 - interaction list now populated by a list of scanned substances is processed |
| 60 - retrieve drug data and drug interaction data for each of the scanned substances and determine relative interactions between substances |
| 70 - receive genetic scans for subjects |
| 80 – apply pharmacogenomic information to the drug-drug interaction data and select the best medication and identify people who need an unusually high or low dose |
| 90 - relative interactions can be rendered within a report such as a paper report or a graphical user interface display |

| |
|---|
| 110 - image of a substance such as a drug can be acquired |
| 120 - identify content for the substance can be retrieved from the image |
| 130 - substance can be identified according to the identifying content |
| 140 - identified substance can be added to an interaction list |
| 150 - if additional substances remain to be imaged, loop back to 310 |
| 160 - receive genetic scans for subjects |
| 170 – retrieve drug data and drug interaction data for each of the imaged substances and determine relative interactions between substances |
| 180 - apply pharmacogenomic information to the drug-drug interaction data and select the best medication |
| 190 - relative interactions can be rendered within a report such as a paper report or a graphical user interface display |

| |
|---|
| 10 – perform reading of substance content from RF tag or barcode on a secure bottle |
| 20 – cryptographically identify content for the substance |
| 30 - identified substance can be added to an interaction list |
| 40 - if additional substances remain to be scanned (RF/Bar Code), loop back to 10 |
| 50 - interaction list now populated by a list of scanned substances is processed |
| 60 - retrieve drug data and drug interaction data for each of the scanned substances and determine relative interactions between substances |
| 70 – receive genetic scans for subjects |
| 80 – apply pharmacogenomic information to the drug-drug interaction data and select the best medication and identify people who need an unusually high or low dose |
| 90 - relative interactions can be rendered within a report such as a paper report or a graphical user interface display |

FIG. 1A

| |
|---|
| 110 - image of a substance such as a drug can be acquired |
| 120 - identify content for the substance can be retrieved from the image |
| 130 - substance can be identified according to the identifying content |
| 140 - identified substance can be added to an interaction list |
| 150 - if additional substances remain to be imaged, loop back to 310 |
| 160 - receive genetic scans for subjects |
| 170 – retrieve drug data and drug interaction data for each of the imaged substances and determine relative interactions between substances |
| 180 – apply pharmacogenomic information to the drug-drug interaction data and select the best medication |
| 190 - relative interactions can be rendered within a report such as a paper report or a graphical user interface display |

FIG. 1B

| |
|---|
| 310 - construct a comprehensive gene-drug-drug interactions (GDDIs) training dataset that includes all pharmaceutical, pharmacokinetic (PK), pharmacogenetic (PG), and pharmacodynamic (PD) GDDIs from multiple data sources for each drug in a set of drugs used by a plurality of subjects |
| 320 - construct side effect features for each of the drugs in the set from genetic panels for an individual and side effects associated with the drugs in the set |
| 330 - build, using the GDDIs training dataset, a GDDIs classifier for predicting whether or not a given drug pair derived from the set of drugs results in adverse interactions, and repeat this process for all possible drug pairs derivable from the set of drugs |
| 340 - obtain predicted GDDIs a trained classifier such as a deep learning machine (FIG. 4) |
| 350 - for each side effect, build data structure with side effect features and perform test to determine whether that side effect is differentially shown between positive predicted GDDIs and negative predicted GDDIs |
| 380 – determine relative interactions between the different drug substances by locating references in the interaction data for each of the drug substances to others of the substances |
| 390 render the relative interactions within a report such as a paper report or a graphical user interface display |

FIG. 3

PHARMACOGENETIC DRUG INTERACTION MANAGEMENT SYSTEM

BACKGROUND

The present invention relates to the field of computerized drug identification.

Drug interactions remain a principal aspect of the pharmaceutical sciences. A drug interaction is a commonly known situation in which a substance affects the activity of a drug, such that the effects of a given drug is increased or decreased, or the combination of the substance and the drug produce a new effect that neither produces alone. Typically, drug-drug interactions are most unpredictable; however, drug-food interactions also are known to exist between drugs and foods, as well as drug-herb interactions between drugs and herbs.

Generally speaking, it is desirable to avoid drug interactions due to the possibility of a poor or unexpected outcome resulting from the interaction of a drug with another substance. Consequently, known drug interactions often are listed in the literature distributed with a drug. Providing an exhaustive list of drug interactions in literature, however, can be difficult when a substantial number of drug interactions are known to exist. As such, voluminous books have been created as an aggregation of known drug interactions. While the most diligent review of a book of known drug interactions will reveal the requisite information necessary to avoid an undesirable outcome from a drug interaction of a prescribed selection of drugs, in practice it is not reasonable to presume that a dispensary of drugs will consult the requisite literature when dispensing a drug.

SUMMARY

In one aspect, a system includes a substance to be consumed by a subject and one or more indicia labeling the substance with: genomic biomarkers; drug exposure and clinical response variability; risk for adverse events; genotype-specific dosing; polymorphic drug target and disposition genes; and treatment based on the biomarker.

Advantages of the system may include one or more of the following. The system may make medical trials more efficient. This will lower the costs that come about due to adverse drug side effects and prescription of drugs that have been proven ineffective in certain genotypes. Drug companies can develop and license a drug specifically intended for those who are the small population genetically at risk for adverse side effects.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein:

FIGS. 1A-1B show exemplary substance interaction management processes;

DETAILED DESCRIPTION OF THE INVENTION

Figure 2:
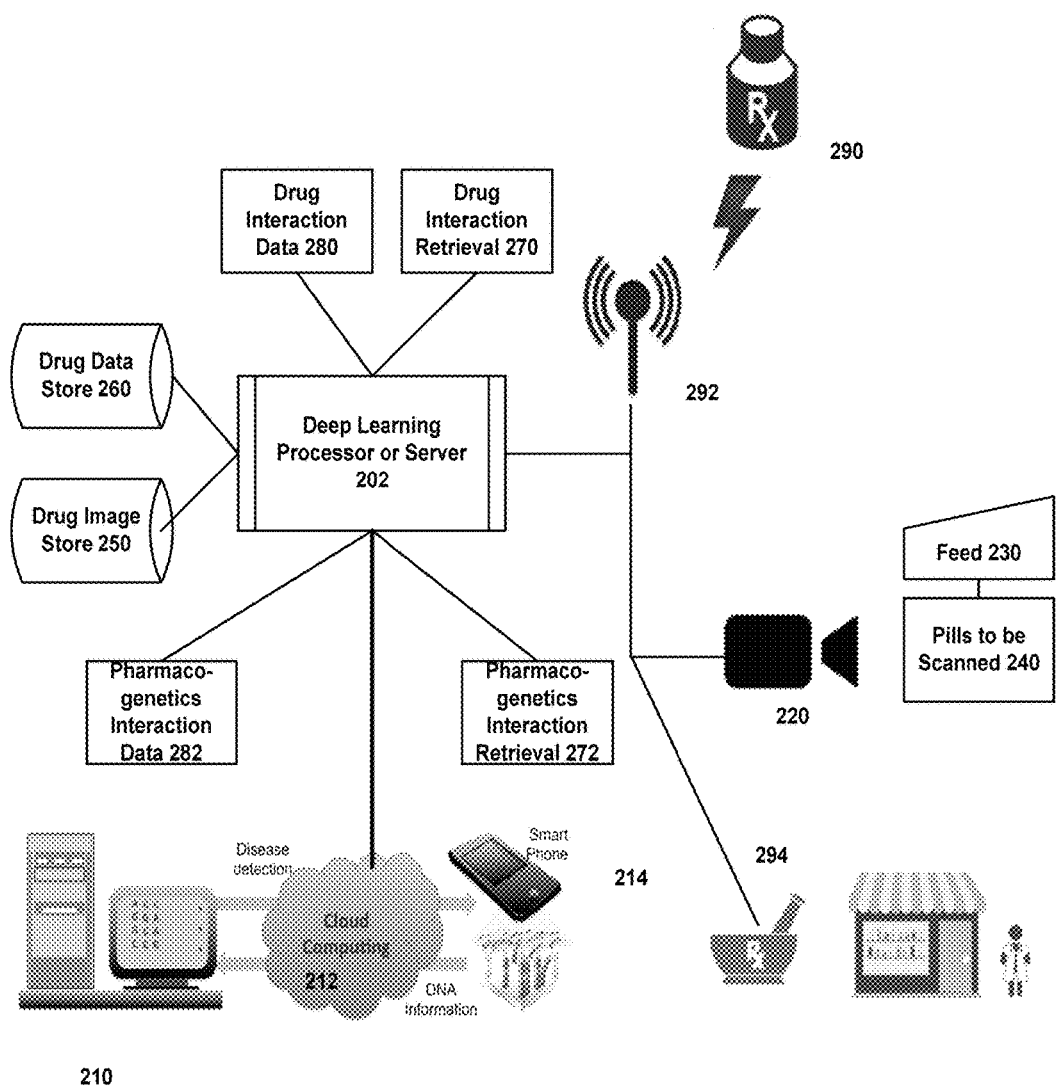
FIG. 2 is a schematic illustration of a data processing system configured for computer management genetic information, precision medication and drug interaction information retrieval; and, FIG. 3 is a flow chart illustrating a process for pharmacogenetics drug interaction information retrieval.

Embodiments of the present invention provide a method, system and computer program product for computer identification (scanning or imaging of drugs) for drug interaction information retrieval. In accordance with an embodiment of the present invention, multiple different drugs can be scanned or imaged to detect identifiable content disposed on the different drugs. Each drug can be compared to a data store of drug information to identify each drug. Thereafter, pharmacogenetics data and drug interaction data can be retrieved for each identified drug. Further, known drug-drug interactions and genetic impacts for the identified drugs can be determined and a report can be provided to include the known drug-drug interactions. In this way, precision medicine and drug-drug interactions resulting from the use of the multiple different drugs can be determined without recourse to a voluminous text of drug interactions.

In illustration, FIGS. 1A-1B show exemplary processes for computer detection of substances or drugs for drug interaction information retrieval. As shown in FIG. 1A, in 10, the process cryptographically reads substance content from RF tag or barcode on a secure bottle and in 20 identifies content for the substance. In 30, identified substances are added to an interaction list and in 40 the process determines if additional substances remain to be scanned (RF/Bar Code), and if so loops back to 10. In 50, the interaction list now populated by a list of scanned substances is processed. Next, in 60 the process retrieves drug data and drug interaction data for each of the scanned substances and determines relative interactions between substances. In 70, the process receives genetic scans for subjects. In 80, the process applies pharmacogenomic information to the drug-gene interaction data and selects the best medication and identify people who need an unusually high or low dose. In 90, relative interactions can be rendered within a report such as a paper report or a graphical user interface display.

Turning now to FIG. 1B, a camera based drug identification and drug interaction management system is shown. In 110, images of a substance such as a drug can be acquired. In 120 the process identifies content for the substance can be retrieved from the image. In 130, substances can be identified according to the identifying content. In 140, the identified substance can be added to an interaction list. In 150 the process loops back to 110 if additional substances remain to be imaged and if not, the interaction list now populated by a list of imaged substances can be processed. In 160, the process receives genetic scans for subjects. In 170, the process retrieves drug data and drug interaction data for each of the imaged substances and determines relative interactions between substances, and in 180 pharmacogenomic information is applied to select the best medication and identify people who need an unusually high or low dose. In 190, the relative interactions can be rendered within a report such as a paper report or a graphical user interface display.

The process shown in FIGS. 1A-1B can be implemented within a data processing system. In further illustration, FIG. 2 schematically depicts a data processing system configured for computer visualization of drugs for drug interaction information retrieval. The system can include a host computing platform 202 coupled to a camera 220 such as a digital still camera or digital video camera. The camera 220 can be focused on a marshalling point 240 provided by a marshalling apparatus 230, for example gravity feed or isolation chamber or miniature conveyor belt. The host computing platform 202 also can be communicatively coupled a drug image data store 250 of known substances and corresponding known identifying content visually disposed on the known substances. The host computing platform 202 additionally can be communicatively coupled to a drug interaction data store 260 providing drug interaction data for different substances relative to other substances including prescription and over-the-counter drugs, vitamins and herbal remedies, and food products.

In one embodiment of FIG. 2, multiple different substances such as prescription drugs, over-the-counter drugs or even vitamins and herbal remedies can be provided to a marshalling apparatus such as a gravity feed or miniature conveyor belt or even a chamber. The marshalling apparatus can isolate an individual one of the different substances for imaging by camera 220, for example a charge coupled device (CCD) driven digital camera or video recorder. The camera 220 can capture an image of each individual one of the different substances 110A, 110B, 110N and computer visualization for drug interaction information retrieval logic 300 can process each captured image to detect identifying content disposed on each of the different substances such as a pill marking or code. The computer visualization for drug interaction information retrieval logic 300 in turn can compare the identified content to a data store of known substances 140 to identify each of the different substances. The computer can lookup not only known drug interactions for each of the different substances, but also known drug interactions between the identified ones of the substances and pharmacogenetics impact on the individual patient. Thereafter, a drug interaction report can be produced indicating the known drug interactions between the identified ones of the substances.

The host computing platform 202 can support the execution of computer scanning or visualization for drug interaction information retrieval logic 270. The logic can include program code enabled to acquire imagery of different substances in the marshalling point 240. The program code further can be enabled to locate and retrieve identifying content disposed on the different substances and to look up the identifying content in the drug image data store 250 in order to identify each of the substances. The program code yet further can be enabled to retrieve from drug interaction data store 260 drug interactions for each of the identified substances and to particularly correlate the retrieved drug interactions to different ones of the substances so that relative drug interactions can be determined for the substances. Finally, the program code can be enabled to render a report of drug interaction data in a graphical user interface display 280 of drug interaction data.

The computing platform 202 also receives pharmacogenetics interaction 282. Notably, the host computing platform 202 can support the execution of computer visualization for pharmacogenetics interaction information retrieval logic 272. Genetic information is captured by high speed gene sequencing machine 210 that uploads gene data to a cloud computing network 212. The doctors, pharmacists, or consumers can access DNA information using mobile computers such as smart phone 214, for example.

The system can have wireless communication 292 with the medication's labels. For example, the labels can have RF tags or NFC tags that provide upon inquiry FDA required labeling contents. In one embodiment, the content can be genomic biomarkers; drug exposure and clinical response variability; risk for adverse events; genotype-specific dosing; polymorphic drug target and disposition genes; and treatment based on the biomarker. NFC tags are passive devices and operate without a power supply of their own and are reliant on an active device to come into range before they are activated. To power these NFC tags, electromagnetic induction is used to create a current in the passive device. Active devices, such as a reader or a smartphone, are responsible for generating the magnetic field with a simple coil of wire, which produces magnetic fields perpendicular to the flow of the alternating current in the wire. To reduce power, NFC operates over just a few inches, rather than the meters in other types of wireless communication.

The system can be used to provide personalized medicine through custom pharmacy compounding 294 or custom production of a drug whose various properties (e.g. dose level, ingredient selection, route of administration, etc.) are selected and crafted for an individual patient (in contrast to mass-produced unit doses or fixed-dose combinations).

The genetic scan in 70 can be generated by gene sequencing machines. DNA sequencing is the process of determining the precise order of nucleotides within a DNA molecule. It includes any method or technology that is used to determine the order of the four bases—adenine, guanine, cytosine, and thymine—in a strand of DNA. Various high speed sequencers can be used. For example, Nanopore DNA sequencing is based on the readout of electrical signals occurring at nucleotides passing by alpha-hemolysin pores covalently bound with cyclodextrin. The DNA passing through the nanopore changes its ion current. Oxford Nanopore Technologies offers a handheld sequencer capable of generating more than 150 megabases of sequencing data in one run.

Another approach uses measurements of the electrical tunnelling currents across single-strand DNA as it moves through a channel. Depending on its electronic structure, each base affects the tunnelling current differently, allowing differentiation between different bases. The use of tunnelling currents has the potential to sequence orders of magnitude faster than ionic current methods and the sequencing of several DNA oligomers and micro-RNA has already been achieved. Sequencing by hybridization is a non-enzymatic method that uses a DNA microarray. A single pool of DNA whose sequence is to be determined is fluorescently labeled and hybridized to an array containing known sequences. Strong hybridization signals from a given spot on the array identify its sequence in the DNA being sequenced. Mass spectrometry may be used to determine DNA sequences.

Matrix-assisted laser desorption ionization time-of-flight mass spectrometry, or MALDI-TOF MS, has specifically been investigated as an alternative method to gel electrophoresis for visualizing DNA fragments. With this method, DNA fragments generated by chain-termination sequencing reactions are compared by mass rather than by size. The mass of each nucleotide is different from the others and this difference is detectable by mass spectrometry. Single-nucleotide mutations in a fragment can be more easily detected with MS than by gel electrophoresis alone. MALDI-TOF MS can more easily detect differences between RNA fragments, so researchers may indirectly sequence DNA with MS-based methods by converting it to RNA first. In microfluidic Sanger sequencing the entire thermocycling amplification of DNA fragments as well as their separation by electrophoresis is done on a single glass wafer (approximately 10 cm in diameter) thus reducing the reagent usage as well as cost. Microscopy-based technique directly visualizes the sequence of DNA molecules using electron microscopy. RNAP sequencing is based on use of RNA polymerase (RNAP), which is attached to a polystyrene bead. One end of DNA to be sequenced is attached to another bead, with both beads being placed in optical traps. RNAP motion during transcription brings the beads in closer and their relative distance changes, which can then be recorded at a single nucleotide resolution. The sequence is deduced based on the four readouts with lowered concentrations of each of the four nucleotide types, similarly to the Sanger method. Other high speed gene sequencers can be used.

The system applies pharmacogenomic information to select the best medication and identify people who need an unusually high or low dose. This is in addition to clinical factors, such as a patient's age, weight, sex, and liver and kidney function. Pharmacogenomics (sometimes called pharmacogenetics) is focused on understanding how genes affect individual responses to medications and to help doctors select the drugs and dosages best suited for each person. Pharmacogenomics looks at variations in genes for proteins that influence drug responses. Such proteins include a number of liver enzymes that convert medications into their active or inactive forms. Even small differences in the genetic sequences of these enzymes can have a big impact on a drug's safety or effectiveness. One example involves a liver enzyme known as CYP2D6. This enzyme acts on a quarter of all prescription drugs, including the painkiller codeine, which it converts into the drug's active form, morphine. The CYP2D6 gene exists in more than 160 different versions, many of which vary by only a single difference in their DNA sequence, although some have larger changes. The majority of these variants don't affect drug responses. Some people have hundreds or even thousands of copies of the CYP2D6 gene (typically, people have two copies of each gene). Those with extra copies of this gene manufacture an overabundance of CYP2D6 enzyme molecules and metabolize the drug very rapidly. As a result, codeine may be converted to morphine so quickly and completely that a standard dose of the drug can be an overdose. On the other end of the spectrum, some variants of CYP2D6 result in a nonfunctional enzyme. People with these variants metabolize codeine slowly, if at all, so they might not experience much pain relief. For these people, doctors might prescribe a different type of pain reliever. Pharmacogenomic information can cover dosage guidance, possible side effects or differences in effectiveness for people with certain genomic variations—can help doctors tailor their drug prescriptions for individual patients. The system applies pharmacogenomic data to develop and market drugs for people with specific genetic profiles. The system can identify the genetic basis for certain serious side effects, drugs could be prescribed only to people who are not at risk for them. As a result, potentially lifesaving medications, which otherwise might be taken off the market because they pose a risk for some people, could still be available to those who could benefit from them. For example, a few drug and gene associations are listed in the Appendix.

It will be recognized by the skilled artisan that while the computer visualization for drug interaction information retrieval logic 270 is shown to execute in a single host computing platform 202, the invention is not so limited and the computer visualization for drug interaction information retrieval logic 270 also can be distributed in form across multiple different computing platforms. Further, the camera 220 and marshalling apparatus 230 can be located remotely from the host computing platform 202 whilst providing acquired imagery to the host computing platform 210 over a computer communications network, whether wireless or wirebound. Yet further, either or both of the drug image data store 250 and the drug interaction data store 260 can be remotely disposed from the host computing platform 202 and accessible over a computer communications network, whether wireless or wirebound.

The system enables a medical model that separates patients into different groups—with medical decisions, practices, interventions and/or products being tailored to the individual patient based on their predicted response or risk of disease.

Having the ability to look at a patient on an individual basis will allow for a more accurate diagnosis and specific treatment plan. Genotyping is the process of obtaining an individual's DNA sequence by using biological assays. By having a detailed account of an individual's DNA sequence, their genome can then be compared to a reference genome, like that of the Human Genome Project, to assess the existing genetic variations that can account for possible diseases. An individual's genetic make-up also plays a large role in how well they respond to a certain treatment, and therefore, knowing their genetic content can change the type of treatment they receive. The system applies pharmacogenomics by using an individual's genome to provide a more informed and tailored drug prescription. Often, drugs are prescribed with the idea that it will work relatively the same for everyone, but in the application of drugs, there are a number of factors that must be considered. The detailed account of genetic information from the individual will help prevent adverse events, allow for appropriate dosages, and create maximum efficacy with drug prescriptions. The pharmacogenomic process for discovery of genetic variants that predict adverse events to a specific drug has been termed toxgnostics.

In addition to specific treatment, personalized medicine can greatly aid the advancements of preventive care. For instance, many women are already being genotyped for certain mutations in the BRCA1 and BRCA2 gene if they are predisposed because of a family history of breast cancer or ovarian cancer. As more causes of diseases are mapped out according to mutations that exist within a genome, the easier they can be identified in an individual. Measures can then be taken to prevent a disease from developing. Even if mutations were found within a genome, having the details of their DNA can reduce the impact or delay the onset of certain diseases. Having the genetic content of an individual will allow better guided decisions in determining the source of the disease and thus treating it or preventing its progression. This will be extremely useful for diseases like Alzheimer's or cancers that are thought to be linked to certain mutations in human DNA.

The system can be used to test efficacy and safety of a drug specific to a targeted patient group/sub-group is companion diagnostics. This technology is an assay that is developed during or after a drug is made available on the market and is helpful in enhancing the therapeutic treatment available based on the individual. These companion diagnostics have incorporated the pharmacogenomic information related to the drug into their prescription label in an effort to assist in making the most optimal treatment decision possible for the patient.

Having an individual's genomic information can be significant in the process of developing drugs as they await approval from the FDA for public use. Having a detailed account of an individual's genetic make-up can be a major asset in deciding if a patient can be chosen for inclusion or exclusion in the final stages of a clinical trial. Being able to identify patients who will benefit most from a clinical trial will increase the safety of patients from adverse outcomes caused by the product in testing, and will allow smaller and faster trials that lead to lower overall costs. In addition, drugs that are deemed ineffective for the larger population can gain approval by the FDA by using personal genomes to qualify the effectiveness and need for that specific drug or therapy even though it may only be needed by a small percentage of the population. Treatments can be more specifically tailored to an individual and give insight into how their body will respond to the drug and if that drug will work based on their genome. The personal genotype can allow physicians to have more detailed information that will guide them in their decision in treatment prescriptions, which will be more cost-effective and accurate.

FIG. 3 shows a method 300 for predicting drug-drug interactions based on genetic data and clinical side effects, in accordance with an embodiment of the present principles. The process includes the following: At 310, construct a comprehensive gene-drug-drug interactions (GDDIs) training dataset that includes all pharmaceutical, pharmacokinetic (PK), pharmacogenetic (PG), and pharmacodynamic (PD) GDDIs from multiple data sources for each drug in a set of drugs under consideration. In an embodiment, the multiple data sources can include, but are not limited to, the following: gene sequencers, clinical trials; drug development information; empirical information; a drug bank; drug label information; an adverse event reporting system (e.g., the FDA Adverse Event Reporting System information (FAERS)); and text mining from scientific documents (e.g., search tool for interactions of chemicals (STITCH)). At step 320, construct side effect features for each of the drugs in the set from genetic panels for an individual and side effects associated with the drugs in the set. In an embodiment, the genetic panels are generated by genetic sequencers, and all drugs' side effects, from which the side effect features are constructed, come from one or more of the following sources: clinical trials; drug development; empirical information; FDA drug label (SIDER and DAILYMED®); FDA Adverse Event Reporting System (FAERS); and real-world evidence. At 330, build, using the GDDIs training dataset, a GDDIs classifier for predicting whether or not a given drug pair derived from the set of drugs results in adverse interactions, and repeat this process for all possible drug pairs derivable from the set of drugs. In an embodiment, the features used for building the classifier can include, but are not limited to, the following: drug's clinical side effect keywords; and other drug properties (e.g., chemical structures, protein targets, and so forth).

At 340, obtain predicted GDDIs from the classifier. At 350, for each side effect, perform statistical test to determine whether that side effect is differentially shown between positive predicted GDDIs and negative predicted GDDIs. In one embodiment, the term "positive predicted GDDIs" refers to drugs pairs that cannot be taken together given a patient genetic profile. In contrast, the term "negative predicted GDDIs" refers to drugs pairs that may be safe to use together with a genetic profile.

Side effects are effects after taking a medicine, which are other than the intended therapeutic effects. Label side effects means the side effects are recorded in drug labels (for example, but not limited to, SIDER database, DAILYMED®, and so forth). FDA side effects means the side effects are recorded in, for example, but not limited to, the FDA Adverse Event Reporting System (FAERS). Consider, for example, the drug Ibuprofen as an example, DAILYMED® records its 249 types of label side effects (e.g., abdominal discomfort, confusion, dry mouth, vomiting, and weight loss), and FAERS records its 728 types of FDA side effects (e.g., anxiety, ear ache, fatigue, tooth loss, sleep disorder).

In 380, relative interactions between the different drug substances can be determined by locating references in the interaction data for each of the drug substances to others of the substances. Finally, in block 390, the relative interactions can be rendered within a report such as a paper report or a graphical user interface display. Optionally, an activatable link can be provided in the display for selected ones of the drug substances for reordering the selected ones of the drug substances. In this way, the relative drug interactions resulting from the dispensing of multiple different drug substances based on patient genetic data can be determined without requiring a tedious manual process of looking up drug interaction data for each substance and manually correlating the drug interaction data for the specific combination of dispensed substances.

The system can also perform GDDI discovery and prediction that uses molecular structure similarity information derived from fingerprint-based modeling. Identifying new GDDIs using structural similarity is based on the basic idea that if drug A interacts with drug B, and drug C is structurally similar to A, then C should also interact with B (the argument also follows if A is replaced with B). Hence, by combining knowledge of known interactions with structural similarity it is possible to identify new interactions. The process uses a list of drug-drug interactions from DrugBank (step 1), structural similarity computation was carried out using molecular fingerprints (step 2), apply gene-drug interaction to similar drugs, and a new list of gene-drug interactions can be inferred.

Structural similarity can be identified in three steps: 1) Collecting and processing drug structures: Information on the structures of the compounds in DrugBank is retrieved along with the SMILE code (a chemical notation representing a chemical structure in linear textual form). 2) Structural representation: BIT_MACCS (MACCS Structural Keys Bit packed) fingerprints are calculated for all molecules included in the study and each molecule is represented as a bit vector that codes the presence or absence of structural features where each feature is assigned a specific bit position. 3) Similarity measures, computation, and data representation: Different measures are used to compare similarity between two molecular fingerprints. In one embodiment, the molecular fingerprints were compared using Tanimoto coefficient (TC). The TC can span values between 0 and 1, where 0 means 'maximum dissimilarity' and 1 means 'maximum similarity.' The TC between two fingerprint representations A and B is defined as the number of features present in the intersection of both fingerprints A and B divided by the number of features present in the union of both fingerprints. Next, for each drug affected by a particular gene, the process predicts new gene based DDIs. One embodiment predicts new DDIs reduces to matrix multiplication of the matrices M1, which consists of the established interactions, and M2, which consists of the similarity matrix.

The pharmacogenomic information can be applied to drug labeling. One embodiment may contain information on genomic biomarkers and can describe:

Drug exposure and clinical response variability
Risk for adverse events
Genotype-specific dosing
Mechanisms of drug action
Polymorphic drug target and disposition genes The information may include specific actions to be taken based on the biomarker information. Pharmacogenomic information can appear in different sections of the labeling depending on the actions. Biomarkers in the table include but are not limited to germ-line or somatic gene variants, functional deficiencies, expression changes, and chromosomal abnormalities; selected protein biomarkers that are used to select patients for treatment are also included.

In one embodiment, the process includes constructing a gene-drug interactions training dataset that includes pharmaceutical, pharmacokinetic or pharmacodynamics, and pharmacogenomics drug-drug interactions for each drug; constructing side effect features for each of the plurality of drugs from side effects associated with the plurality of drugs; running a gene-drug-drug interactions classifier that predicts adverse drug-drug interactions for drug pairs and the genetic scan; and for each of the side effects, performing a Fisher's exact test to determine predicted gene-drug-drug interactions. Fisher's exact testis a statistical significance test used in the analysis of contingency tables. It is one of a class of exact tests, so called because the significance of the deviation from a null hypothesis (e.g., P-value) can be calculated exactly, rather than relying on an approximation that becomes exact in the limit as the sample size grows to infinity, as with many statistical tests.

Figure 4:
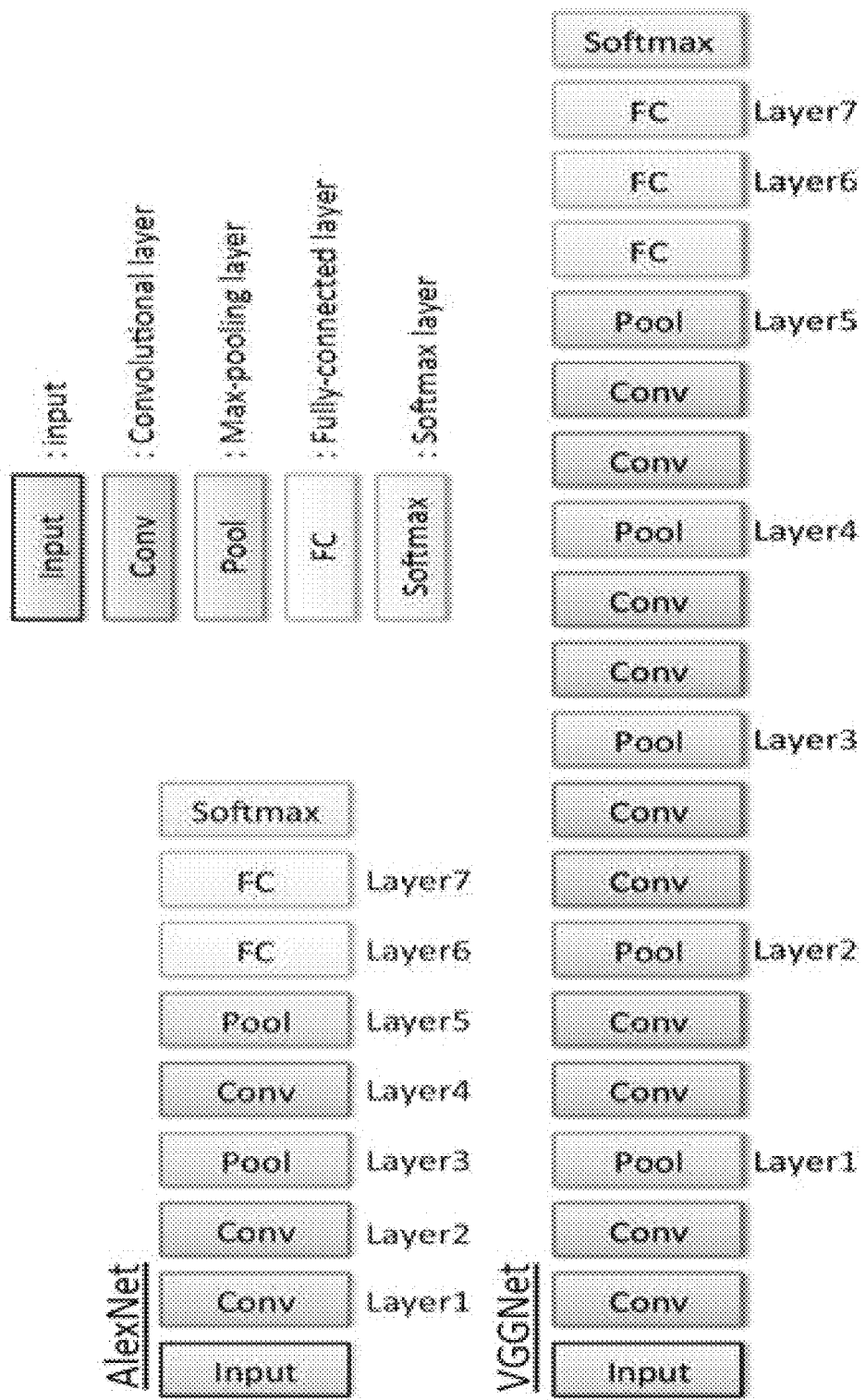
FIG. 4 shows a big data learning machine to process genetic data and determine pharmacogenetics relationship among genes and drugs for drug interaction purposes.

FIG. 4 shows a deep learning machine using deep convolutionary neural networks for detecting genetic based drug-drug interaction. One embodiment uses an AlexNet: 8-layer architecture, while another embodiment uses a VGGNet: 16-layer architecture (each pooling layer and last 2 FC layers are applied as feature vector). For drugs, the indications of use and other drugs used capture most of many important covariates. One embodiment access data from SIDER (a text-mined database of drug package inserts), the Offsides database that contains information complementary to that found in SIDER and improves the prediction of protein targets and drug indications, and the Twosides database of mined putative DDIs also lists predicted adverse events, all available at the http://PharmGKB.org Web site.

The system of FIG. 4 receives data on adverse events strongly associated with indications for which the indication and the adverse event have a known causative relationship. A drug-event association is synthetic if it has a tight reporting correlation with the indication ($\rho \geq 0.1$) and a high relative reporting (RR) association score (RR$\geq$2). Drugs reported frequently with these indications were 80.0 (95% CI, 14.2 to 3132.8; P<0.0001, Fisher's exact test) times as likely to have synthetic associations with indication events. Disease indications are a significant source of synthetic associations. The more disproportionately a drug is reported with an indication (x axis), the more likely that drug will be synthetically associated. For example, adverse events strongly associated with drugs are retrieved from the drug's package insert. These drug-event pairs represent a set of known strong positive associations.

Adverse events related to sex and race are also analyzed. For example, for physiological reasons, certain events predominantly occur in males (for example, penile swelling and azoospermia). Drugs that are disproportionately reported as causing adverse events in males were more likely to be synthetically associated with these events. Similarly, adverse events that predominantly occur in either relatively young or relatively old patients are analyzed.

"Off-label" adverse event data is also analyzed, and off-label uses refer to any drug effect not already listed on the drug's package insert. For example, the SIDER database, extracted from drug package inserts, lists 48,577 drug-event associations for 620 drugs and 1092 adverse events that are also covered by the data mining. Offsides recovers 38.8% (18,842 drug-event associations) of SIDER associations from the adverse event reports. Thus, Offsides finds different associations from those reported during clinical trials before drug approval.

Polypharmacy side effects for pairs of drugs (Twosides) are also analyzed. These associations are limited to only those that cannot be clearly attributed to either drug alone (that is, those associations covered in Offsides). The database contains an significant associations for which the drug pair has a higher side-effect association score, determined using the proportional reporting ratio (PRR), than those of the individual drugs alone. The system determines pairwise similarity metrics between all drugs in the Offsides and SIDER databases. The system can predict shared protein targets using drug-effect similarities. The side-effect similarity score between two drugs is linearly related to the number of targets that those drugs share.

The system can determine relationships between the proportion of shared indications between a pair of drugs and the similarity of their side-effect profiles in Offsides. The system can use side-effect profiles to suggest new uses for old drugs. While the preferred system predicts existing therapeutic indications of known drugs, the system can recommend drug repurposing using drug-effect similarities in Offsides.

Corroboration of class-wide interaction effects with EMRs. The system can identify DDIs shared by an entire drug class. The class-class interaction analysis generates putative drug class interactions. The system analyzes laboratory reports commonly recorded in EMRs that may be used as markers of these class-specific DDIs.

The system can be used systematic drug surveillance. The FDA manages a collection of adverse drug event reports to monitor the safety of drugs. They rely on physicians, pharmaceutical companies, and patients to volunteer these reports. Since reporting is not mandatory, many adverse drug events that occur are never reported to the FDA. To address this issue, an embodiment of the present invention uses an algorithm to infer unreported adverse drug events. This embodiment relies on the fact that many adverse events occur together. For example, nausea and vomiting commonly manifest together. Therefore, if a drug is observed to causes nausea, it can be inferred that it also causes vomiting.

The successful prediction of side effects before a drug enters clinical trials can be done. Chemical informatics techniques can predict drug side effects by comparing the structural similarity of drugs. Protein structural similarity is learned by the deep learning system to predict drug side effects. More recently, network and chemical properties are used for predictive models of drug effects and leverage the system's comprehensive database of known drug effects.

In a parallel trend, anti-biotics and cancer treatments have lost their effect over time. As such, even though there is no adverse event, there is still a negative consequence for the patient when the virus/tumor develops resistance to the drug. Thus, the processor can analyze evolutions in the target of the treatment and recommend alternative treatment.

In one aspect, systems and methods includes analyzing a disease state of a subject by collecting genetic profile data on a population of tumors and original tumor treatment(s); identifying one or more evolutionary paths of escape and evolved tumor treatment(s); and based on a subject profile, predicting a probability of escape along the one or more evolutionary paths.

In another aspect, a method for analyzing a disease state of a subject includes capturing a first liquid biopsy from the subject; providing the liquid biopsy to a genetic analyzer to identify the subject's genetic information of a first disease state at a first time point; searching for genetically similar patients and predicting a mutation of the disease into a second disease state at a second time point; analyzing a treatment database and recommending a treatment given the first and second disease states; capturing a second liquid biopsy from the subject at a second time point; providing the second liquid biopsy to the genetic analyzer to identify the subject's genetic information; and if the genetic information from the second time point matches the predicted mutation, continuing the recommended treatment for the subject and otherwise changing the recommended treatment.

In yet another aspect, a method to detect abnormal cellular activities includes sequencing of cell-free nucleic acid with a genetic analyzer or a DNA sequencer; comparing current sequence reads with prior sequence reads from at least two time points; detecting a mutation of the cell-free nucleic acid and updating a diagnostic confidence indication accordingly; and detecting the presence or absence of genetic alteration and/or amount of genetic variation in an individual based on the diagnostic confidence indication of the sequence read.

In a further aspect, a method for analyzing a disease state of a subject includes capturing a first liquid biopsy from the subject; providing the liquid biopsy to a genetic analyzer to identify the subject's genetic information of a first disease state at a first time point; searching for genetically similar subject profiles and predicting a mutation of the disease into a second disease state at a second time point; capturing a second liquid biopsy from the subject; providing the second liquid biopsy to a genetic analyzer to identify the subject's genetic information at a second time point; and if the genetic information from the second time point matches the predicted mutation, continuing the recommended treatment for the subject and otherwise changing the recommended treatment.

In another aspect disclosed herein is a method for analyzing a disease state of a subject by characterizing the subject's genetic information at two or more time points with a genetic analyzer, e.g., a DNA sequencer; and using the information from the two or more time points to produce an adjusted test result in the characterization of the subject's genetic information.

In another aspect, a method detects a trend in the amount of mutation cancer polynucleotides in a sample from a subject over time by determining a frequency of the cancer polynucleotides at a plurality of time points; determining an error range for the frequency at each of the plurality of time points; determining, between an earlier and later time point, whether error ranges (1) overlap, indicating stability of frequency, (2) an increase at the later time point outside the error range, indicating increase in frequency or (3) a decrease at the later time point outside the error range, indicating decrease in frequency.

In yet another aspect, a method detects mutation cellular activities by sequencing of cell-free nucleic acid with a genetic analyzer, e.g., a DNA sequencer; comparing later (e.g., current) sequence reads with prior sequence reads from at least two time points and updating a diagnostic confidence indication accordingly; and detecting the presence or absence of genetic alteration and/or amount of genetic variation in an individual based on the diagnostic confidence indication of the sequence read. A genetic analyzer includes any system for genetic analysis, e.g., by sequencing (DNA sequencer) or hybridization (microarray, fluorescent in situ hybridization, bionanogenomics) or other.

In another aspect, a method detects a mutation in a cell-free or substantially cell free sample obtained from a subject by generating consensus sequences by comparing later (e.g., current) sequence reads by a genetic analyzer, e.g., a DNA sequencer, with prior sequence reads from a prior period and updating a diagnostic confidence indication based on the prior sequence reads, each consensus sequence corresponding to a unique polynucleotide among a set of tagged parent polynucleotides, and generating a genetic profile of extracellular polynucleotides in the subject, wherein the genetic profile comprises a plurality of data resulting from copy number variation or mutation analyses.

In another aspect disclosed herein is a method to detect mutation cellular activities by providing at least one set of tagged parent polynucleotides, and for each set of tagged parent polynucleotides; amplifying the tagged parent polynucleotides in the set to produce a corresponding set of amplified progeny polynucleotides; with a genetic analyzer, e.g., a DNA sequencer, sequencing a subset of the set of amplified progeny polynucleotides, to produce a set of sequencing reads; and collapsing the set of sequencing reads to generate a set of consensus sequences by comparing current sequence reads with prior sequence reads from at least one prior period and updating diagnostic confidence indication accordingly, each consensus sequence corresponding to a unique polynucleotide among the set of tagged parent polynucleotides.

In yet another aspect, a method detects a mutation in a cell-free or substantially cell free sample obtained from a subject by sequencing extracellular polynucleotides from a bodily sample from a subject with a genetic analyzer, e.g., a DNA sequencer; for each of the extracellular polynucleotide, generating a plurality of sequencing reads; filtering out reads that fail to meet a set threshold; mapping sequence reads derived from the sequencing onto a reference sequence; identifying a subset of mapped sequence reads that align with a variant of the reference sequence at each mappable base position; for each mappable base position, calculating a ratio of (a) a number of mapped sequence reads that include a variant as compared to the reference sequence, to (b) a number of total sequence reads for each mappable base position; and comparing current sequence reads with prior sequence reads from at least on other time point and updating a diagnostic confidence indication accordingly.

The method identifies one or more evolutionary paths of escape and evolved tumor treatment(s). These paths are caused by various drivers. For example, as shown in FIG.

Figure 5A:
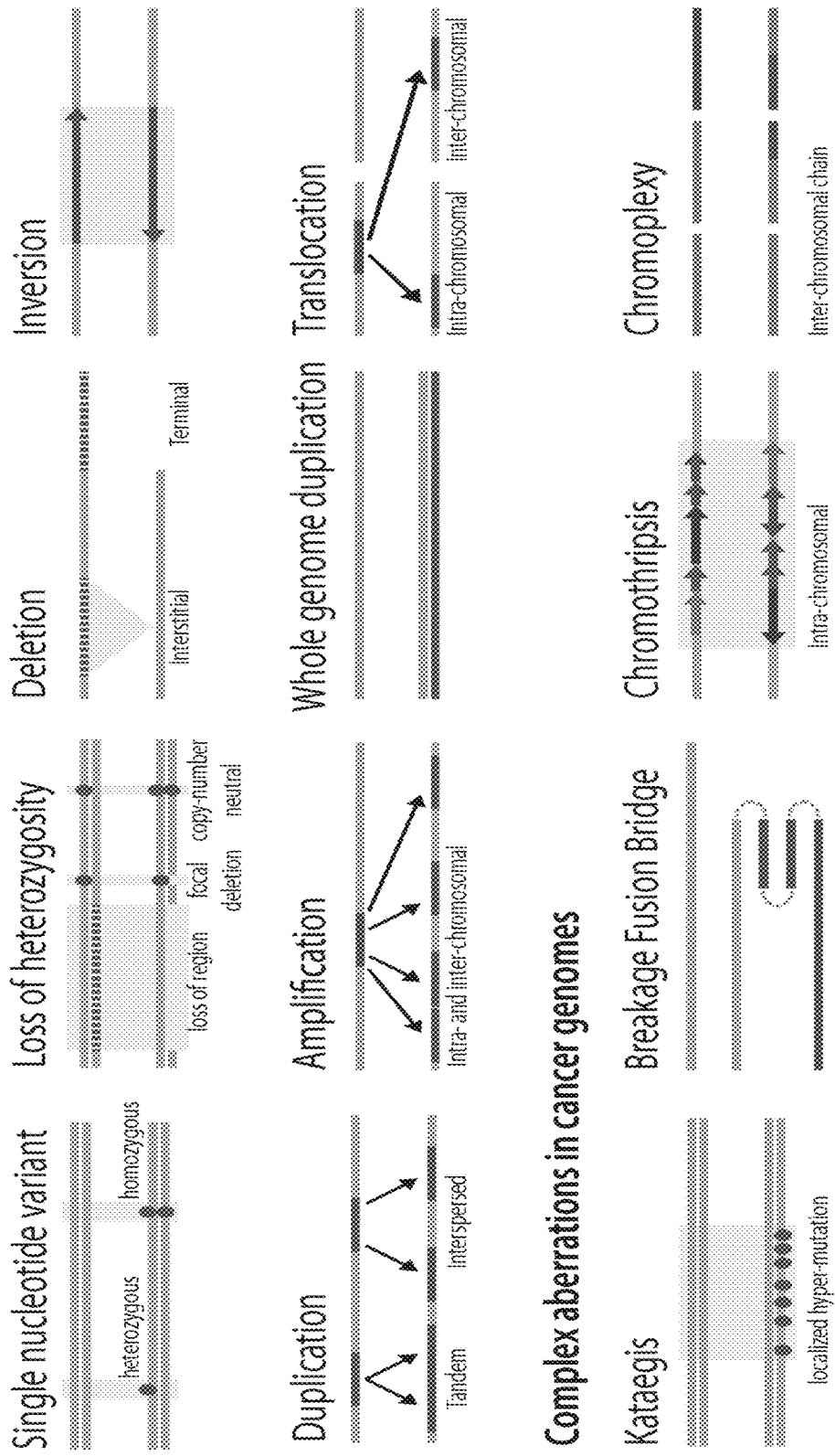
FIG. 5A shows various common aberrations in cancer genomes.

5A, common aberrations in cancer genomes can lead to the abnormal chromosome numbers (aneuploidy) and chromosome structures of a cancer genome. In FIG. 5A, lines indicate the genome with germline genome on top and cancer genome with somatic aberrations below. Double lines are used when differentiating heterozygous and homozygous changes is useful. Dots represent single nucleotide changes, whereas lines and arrows represent structural changes.

Figure 5B:
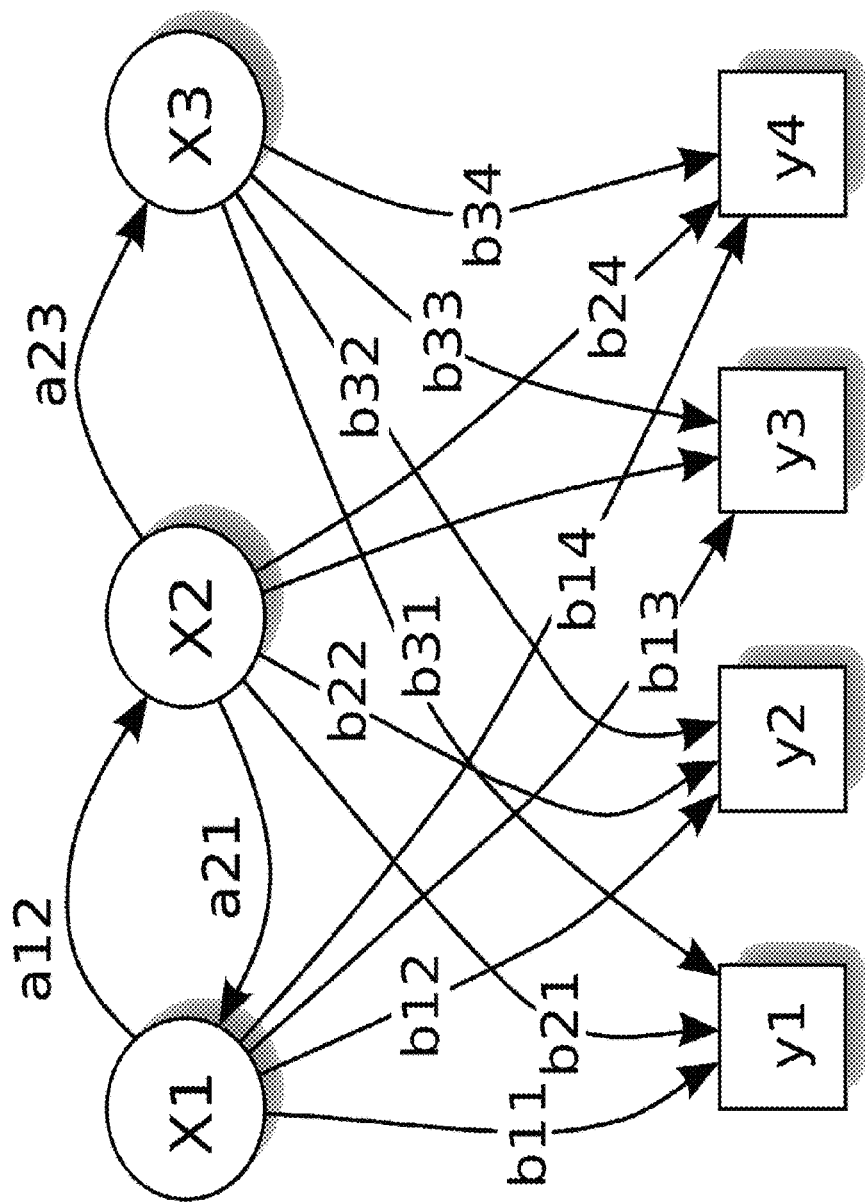
FIG. 5B shows an exemplary system to detect the evolutionary paths of escape.

FIG. 5B shows an exemplary system to detect the evolutionary paths of escape. The system can be a Hidden Markov model (HMM), which is is a statistical Markov model in which the system being modeled is assumed to be a Markov process with unobserved (hidden) states. As known to those skilled in the art, an HMM can be presented as the simplest dynamic Bayesian network. In simpler Markov models (like a Markov chain), the state is directly visible to the observer, and therefore the state transition probabilities are the only parameters. In a hidden Markov model, the state is not directly visible, but output, dependent on the state, is visible. Each state has a probability distribution over the possible output tokens. Therefore the sequence of tokens generated by an HMM gives some information about the sequence of states. A hidden Markov model can be considered a generalization of a mixture model where the hidden variables (or latent variables), which control the mixture component to be selected for each observation, are related through a Markov process rather than independent of each other. As shown in FIG. 5B, the HMM is typically defined by a set of hidden states, a matrix of state transition probabilities and a matrix of emission probabilities. Each hidden state has different statistical properties.

Mutations and genetic alterations including in copy number, for example, allelic imbalances, chromosomal copy number changes, such as amplifications, deletions, aneuploidy, loss of heterozygosity, and micro-satellite instability are often found to be associated with a disease state, for example, cancer. It has been observed that alterations in chromosomal copy number and loss of heterozygosity (LOH) are forms of genetic changes that often signal the activation of oncogenes and inactivation of tumor suppressor genes (anti-oncogenes). Variations in the form of copy number polymorphisms (CNP) can also occur in normal individuals. Identification of the loci implicated in these aberrations can generate anchor points which facilitate oncogenomics and toxicogenomics studies. Subsequently the shared LOH and aberrant CN regions can be used to partition the transcriptome data and track the differential transcript expression in the affected genomic segments. Locating and exploring such alteration events is an important research approach toward understanding the cause and progression of disease. For diploid organisms, the abnormal chromosomal state results when the normal diploid distribution is perturbed, resulting in changes that can include, for example, deletions, amplifications and translocations. Deletions can be of a partial chromosome ranging from microdeletions on the order of several kb to macro-deletions of mega bases, entire arms of a chromosome or entire chromosomes. Amplifications can range from partial chromosomal amplifications to gains of a single copy of a chromosome to multiple copy gains of one or more chromosomes. Translocations generally comprise parts of a first chromosome being translocated to another chromosome.

FIG. 5B shows the general architecture of an instantiated HMM for mutation detection. Each oval shape X1, X2, X3 represents a random variable that can adopt any of a number of values. The random variable $x(t)$ is the hidden state at time t ($x(t) \in \{x1, x2, x3\}$). The random variable $y(t)$ is the observation at time t (with $y(t) \in \{y1, y2, y3, y4\}$). The arrows in the diagram (often called a trellis diagram) denote conditional dependencies. The conditional probability distribution of the hidden variable $x(t)$ at time t, given the values of the hidden variable x at all times, depends only on the value of the hidden variable $x(t-1)$: the values at time t-2 and before have no influence. This is called the Markov property. Similarly, the value of the observed variable $y(t)$ representing the mutation conditions only depends on the value of the hidden variable $x(t)$ (both at time t).

In FIG. 5B, the state space of the hidden variables is discrete, while the observations themselves can either be discrete (typically generated from a categorical distribution) or continuous (typically from a Gaussian distribution). The parameters of a hidden Markov model are of two types, transition probabilities and emission probabilities (also known as output probabilities). The transition probabilities control the way the hidden state at time is chosen given the hidden state at time. The hidden state space is assumed to consist of one of possible values, modeled as a categorical distribution. (See the section below on extensions for other possibilities.) This means that for each of the possible states that a hidden variable at time can be in, there is a transition probability from this state to each of the possible states of the hidden variable at time, for a total of transition probabilities. Note that the set of transition probabilities for transitions from any given state must sum to 1. Thus, the matrix of transition probabilities is a Markov matrix. Because any one transition probability can be determined once the others are known, there are a total of transition parameters.

In addition, for each of the possible states, there is a set of emission probabilities governing the distribution of the observed variable at a particular time given the state of the hidden variable at that time. The size of this set depends on the nature of the observed variable. For example, if the observed variable is discrete with possible values, governed by a categorical distribution, there will be separate parameters, for a total of emission parameters over all hidden states. On the other hand, if the observed variable is an -dimensional vector distributed according to an arbitrary multivariate Gaussian distribution, there will be parameters controlling the means and parameters controlling the covariance matrix, for a total of emission parameters. (In such a case, unless the value of is small, it may be more practical to restrict the nature of the covariances between individual elements of the observation vector, e.g. by assuming that the elements are independent of each other, or less restrictively, are independent of all but a fixed number of adjacent elements.).

The HMM method can model a somatic evolution of cancer. The method includes modeling genetic instability, which results in abnormal numbers of chromosomes or aneuploidy, elevated mutation rates, and altered distributions of mutational patterns.

The method can identify one or more cancer mutation drivers. These drivers include those that disrupt cellular signaling pathways essential for multicellular organisms and possible mutations that increase somatic fitness of cancer cells. The method can include identifying dynamics of tumor progression in a population based on interactions with an environment. The method includes collecting repeated genetic observations to enhance statistical inference about the evolution of tumors.

The method includes recommending or providing a therapeutic regimen in anticipation of the one or more escape paths. Diagnosis of cancer can be done by analyzing the genetic variants, even in the presence of noise. The analysis can be based on the frequency of Sequence Variants or Level of CNV and a diagnosis confidence indication or level for detecting genetic variants in the noise range can be established. The process increases the diagnosis confidence using a plurality of measurements to increase confidence of Diagnosis (6), or alternatively using measurements at a plurality of time points to determine whether cancer is advancing, in remission or stabilized. The diagnostic confidence can be used to identify disease states. For example, cell free polynucleotides taken from a subject can include polynucleotides derived from normal cells, as well as polynucleotides derived from diseased cells, such as cancer cells. Polynucleotides from cancer cells may bear genetic variants, such as somatic cell mutations and copy number variants. When cell free polynucleotides from a sample from a subject are sequenced, these cancer polynucleotides are detected as sequence variants or as copy number variants. The relative amount of tumor polynucleotides in a sample of cell free polynucleotides is referred to as the "tumor burden." Measurements of a parameter, whether or not they are in the noise range, may be provided with a confidence interval. Tested over time, one can determine whether a cancer is advancing, stabilized or in remission by comparing confidence intervals over time. Where the confidence intervals do not overlap, this indicates the direction of disease.

In one implementation, using measurements from a plurality of samples collected substantially at once or over a plurality of time points, the diagnostic confidence indication for each variant can be adjusted to indicate a confidence of predicting the observation of the CNV or mutation. The confidence can be increased by using measurements at a plurality of time points to determine whether cancer is advancing, in remission or stabilized. The diagnostic confidence indication can be assigned by any of a number of known statistical methods is assigned and can be based, at least in part, on the frequency at which the measurements are observed over a period of time. For example, a statistical correlation of current and prior results can be done. Alternatively, for each diagnosis, a hidden Markov model can be built, such that a maximum likelihood or maximum a posteriori decision can be made based on the frequency of occurrence of a particular test event from a plurality of measurements or a time points. As part of this model, the probability of error and resultant diagnostic confidence indication for a particular decision can be output as well. In this manner, the measurements of a parameter, whether or not they are in the noise range, may be provided with a confidence interval. Tested over time, one can increase the predictive confidence of whether a cancer is advancing, stabilized or in remission by comparing confidence intervals over time. Two time points can be separated by about a month to about a year, about a year to about 5 years, or no more than about three months.

The HMM detect with high sensitivity genetic variation in a sample of initial genetic material. The methods involve using one to three of the following tools: First, the efficient conversion of individual polynucleotides in a sample of initial genetic material into sequence-ready tagged parent polynucleotides, so as to increase the probability that individual polynucleotides in a sample of initial genetic material will be represented in a sequence-ready sample. This can produce sequence information about more polynucleotides in the initial sample. Second, high yield generation of consensus sequences for tagged parent polynucleotides by high rate sampling of progeny polynucleotides amplified from the tagged parent polynucleotides, and collapsing of generated sequence reads into consensus sequences representing sequences of parent tagged polynucleotides. This can reduce noise introduced by amplification bias and/or sequencing errors, and can increase sensitivity of detection. Third, the noise in the detection of mutations and copy number variations is reduced by comparing prior sample analysis with the current sample and increasing a diagnostic confidence indication if the same mutations and copy number variations have appeared in prior analysis and otherwise decreasing the diagnostic confidence indication if this is the first time the sequence is observed.

Figure 5C:
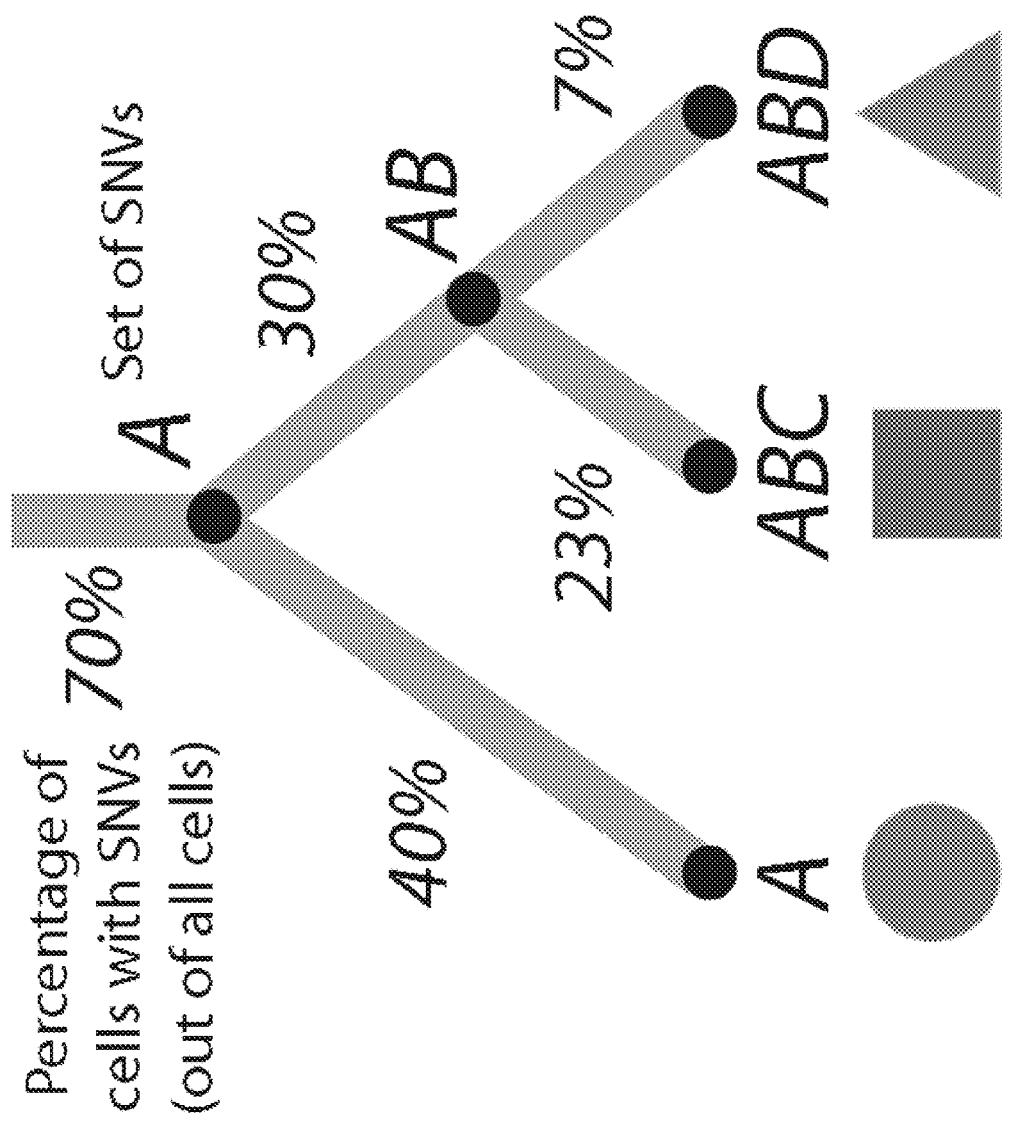
FIG. 5C shows an exemplary model generated by the system of FIG. 5B.

FIG. 5C shows an exemplary model generated by the system of FIG. 2B for inferring tumor phylogeny from next-generation sequencing data. The subclones are related to each other by an evolutionary process of acquisition of mutations. In this example, the three clones (leaf nodes) are characterized by different combinations of the four single nucleotide variant (SNV) sets A, B, C, and D. The percentages on the edges of the tree indicate the fraction of cells with this particular set of SNVs, e.g., 70% of all cells carry A, 40% additionally carry B, and only 7% carry A, B, and D.

Figure 5D:
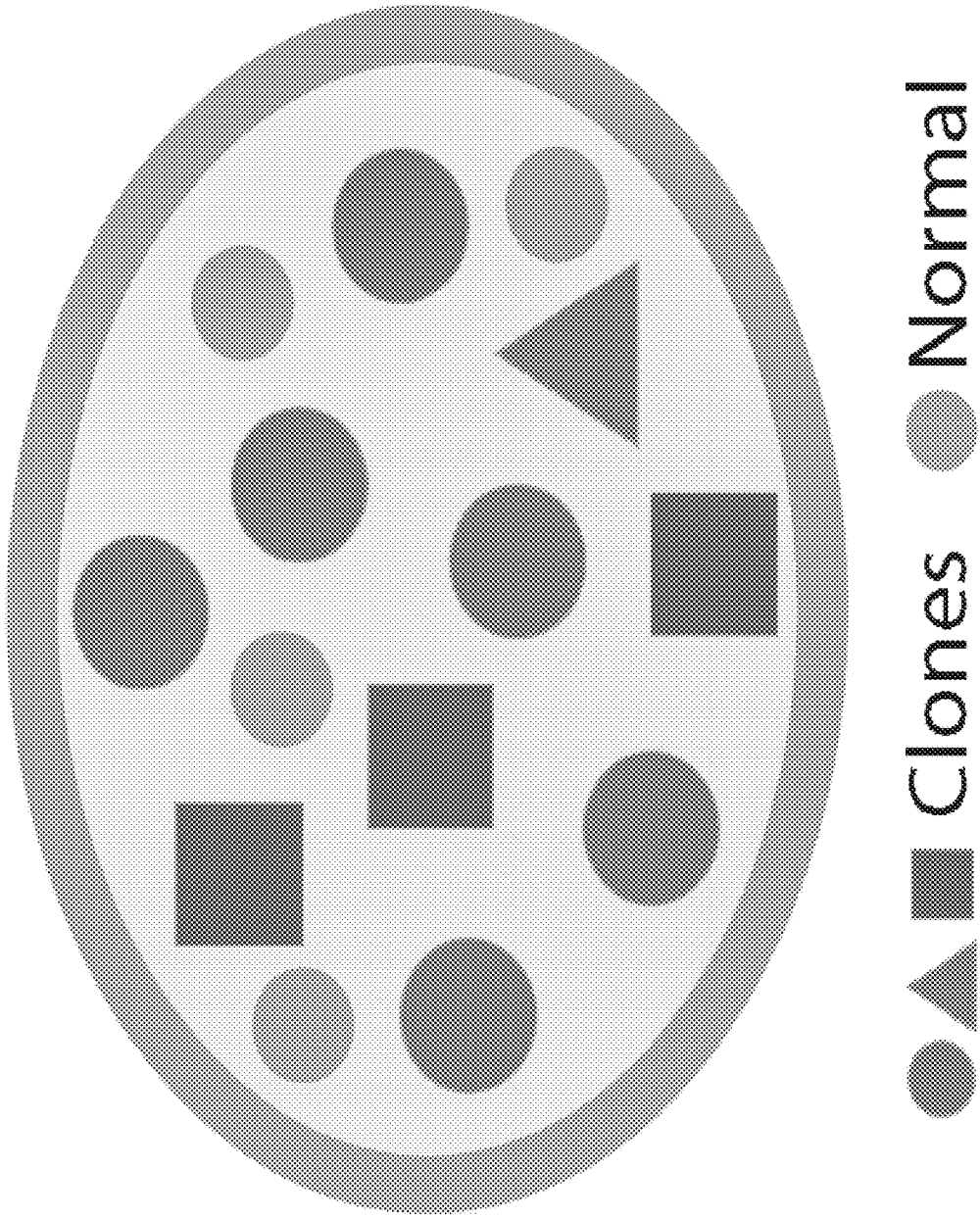
FIG. 5D shows an exemplary a heterogeneous collection of normal cells and cancer subclones developed during an evolutionary history of a tumor.

FIG. 5D shows an exemplary a heterogeneous collection of normal cells and cancer subclones developed during an evolutionary history of a tumor. The evolutionary history of a tumor gives rise to a heterogeneous collection of normal cells (small discs) and cancer subclones (large discs, triangles, squares). Internal nodes that have been fully replaced by their descendants (like the one carrying SNV sets A and B without C or D) are no longer part of the tumor.

Embodiments of the invention can take the form of an entirely hardware embodiment, an entirely software embodiment or an embodiment containing both hardware and software elements. In a preferred embodiment, the invention is implemented in software, which includes but is not limited to firmware, resident software, microcode, and the like. Furthermore, the invention can take the form of a computer program product accessible from a computer-usable or computer-readable medium providing program code for use by or in connection with a computer or any instruction execution system.

For the purposes of this description, a computer-usable or computer readable medium can be any apparatus that can contain, store, communicate, or transport the program for use by or in connection with the instruction execution system, apparatus, or device. The medium can be an electronic, magnetic, optical, electromagnetic, infrared, or semiconductor system (or apparatus or device). Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. Input/output or I/O devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

APPENDIX

| Drug | Therapeutic Area | Biomarker | Referenced Subgroup | Labeling Sections |
|---|---|---|---|---|
| Abacavir | Infectious Diseases | HLA-B | HLA-B*5701 allele carriers | Boxed Warning, Contraindications, Warnings and Precautions |
| Pharmacogenomic Information Ado-Trastuzumab Emtansine | Oncology | ERBB2 | HER2 protein overexpression or gene amplification positive | Indications and Usage, Warnings and Precautions, Adverse Reactions, Clinical Pharmacology, Clinical Studies |
| Pharmacogenomic Information on Afatinib | Oncology | EGFR | EGFR exon 19 deletion or exon 21 substitution (L858R)positive | Indications and Usage, Dosage and Administration, Adverse Reactions, Clinical Pharmacology, Clinical Studies |
| Arntriptyline | Psychiatry | CYP2D6 | CYP2D6 poor metabolizers | Precautions |
| Anastrozole | Oncology | ESR1, PGR | Hormone receptor-positive | Indications and Usage, Adverse Reactions, Drug Interactions, Clinical Studies |
| Arformoterol (1) | Pulmonary | UGT1A1 | UGT1A1 poor metabolizers | Clinical Pharmacology |
| Arformoterol (2) | Pulmonary | CYP2D6 | CYP2D6 intermediate or poor metabolizers | Clinical Pharmacology |
| Aripiprazole | Psychiatry | CYP2D6 | CYP2D6 poor metabolizers | Dosage and Administration, Clinical Pharmacology |
| Pharmacogenomic Information on Arsenic Trioxide | Oncology | PML-RARA | PML-RARα translocation positive | Clinical Pharmacology, Indications and Usage |
| Atomoxetine | Psychiatry | CYP2D6 | CYP2D6 poor metabolizers | Dosage and Administration, Warnings and Precautions, Drug Interactions, Clinical Pharmacology |
| Azathioprine | Rheumatology | TPMT | TPMT intermediate or poor metabolizers | Clinical Pharmacology, Warnings, Precautions Drug Interactions, Adverse Reactions, Dosage and Administration |
| Boceprevir | Infectious Diseases | IFNL3 | IL28B rs12979860 T allele carriers (C/T and T/T genotype) | Clinical Pharmacology |
| Bosutinib | Oncology | BCR/ABL1 | Philadelphia chromosome positive | Indications and Usage Adverse Reactions, Use in Specific Populations, Clinical Studies |
| Busulfan | Oncology | BCR-ABL1 | Philadelphia chromosome negative | Clinical Studies |
| Capecitabine | Oncology | DPYD | DPD deficient | Contraindications, Warnings and Precautions, Patient Information |
| Carbamazepine (1) | Neurology | HLA-B | HLA-B*1502 allele carriers | Boxed Warning, Warnings, Precautions |
| Carbamazepine (2) | Neurology | HLA-A | HLA-A*3101 allele carriers | Warnings |

APPENDIX-continued

| Drug | Therapeutic Area | Biomarker | Referenced Subgroup | Labeling Sections |
|---|---|---|---|---|
| Pharmacogenomic Information on Carglumic Acid | Inborn Errors of Metabolism | NAGS | N-acetylglutamate synthase deficient | Indications and Usage, Warnings and Precautions, Use in Specific Populations Clinical Pharmacology Clinical Studies |
| Carisoprodol | Rheumatology | CYP2C19 | CYP2C19 poor metabolizers | Use in Specific Populations, Clinical Pharmacology |
| Carvedilol | Cardiology | CYP2D6 | CYP2D6 poor metabolizers | Drug Interactions, Clinical Pharmacology |
| Celecoxib | Rheumatology | CYP2C9 | CYP2C9 poor metabolizers | Dosage and Administration, Use in Specific Populations, Clinical Pharmacology |
| Pharmacogenomic Information on Ceritinib | Oncology | ALK | ALK gene rearrangement positive | Indications and Usage, Adverse Reactions, Clinical Pharmacology, Clinical Studies |
| Cetuximab (1) | Oncology | EGFR | EGFR protein expression positive | Indications and Usage, Dosage and Administration, Warnings and Precautions, Adverse Reactions, Clinical Pharmacology, Clinical Studies |
| Cetuximab (2) | Oncology | KRAS | KRAS codon 12 and 13 mutation negative | Indications and Usage, Dosage and Administration, Warnings and Precautions, Adverse Reactions, Clinical Pharmacology, Clinical Studies |
| Cevimeline | Dental | CYP2D6 | CYP2D6 poor metabolizers | Precautions |
| Chloroquine | Infectious Diseases | G6PD | G6PD deficient | Precautions |
| Chlorpropamide | Endocrinology | G6PD | G6PD deficient | Precautions |
| Cisplatin | Oncology | TPMT | TPMT intermediate or poor metabolizers | Clinical Pharmacology, Warnings, Precautions, Adverse Reactions |
| Citalopram (1) | Psychiatry | CYP2C19 | CYP2C19 poor metabolizers | Clinical Pharmacology, Warnings, Dosage and Administration |
| Citalopram (2) | Psychiatry | CYP2D6 | CYP2D6 poor metabolizers | Clinical Pharmacology |
| Clobazam | Neurology | CYP2C19 | CYP2C19 poor metabolizers | Dosage and Administration, Use in Specific Populations, Clinical Pharmacology |
| Clomipramine | Psychiatry | CYP2D6 | CYP2D6 poor metabolizers | Precautions |
| Clopidogrel | Cardiology | CYP2C19 | CYP2C19 intermediate or poor metabolizers | Boxed Warning, Dosage and Administration, Warnings and Precautions, Clinical Pharmacology |
| Clozapine | Psychiatry | CYP2D6 | CYP2D6 poor metabolizers | Dosage and Administration, Use in Specific Populations, Clinical Pharmacology |

APPENDIX-continued

| Drug | Therapeutic Area | Biomarker | Referenced Subgroup | Labeling Sections |
|---|---|---|---|---|
| Codeine | Anesthesiology | CYP2D6 | CYP2D6 ultra-rapid metabolizers | Boxed Warnings, Warnings and Precautions, Use in Specific Populations, Patient Counseling Information |
| Pharmacogenomic Information on Crizotinib | Oncology | ALK | ALK gene rearrangement positive | Indications and Usage, Dosage and Administration, Adverse Reactions, Clinical Pharmacology, Clinical Studies |
| Dabrafenib (1) | Oncology | BRAF | BRAF V600E/K mutation positive | Indications and Usage, Dosage and Administration, Warnings and Precautions, Adverse Reactions, Clinical Pharmacology, Clinical Studies, Patient Counseling Information |
| Dabrafenib (2) | Oncology | G6PD | G6PD deficient | Warnings and Precautions, Adverse Reactions, Patient Counseling Information |
| Dapsone (1) | Dermatology | G6PD | G6PD deficient | Warnings and Precautions, Use in Specific Populations, Patient Counseling Information |
| Dapsone (2) | Infectious Diseases | G6PD | G6PD deficient | Precautions, Adverse Reactions, Overdosage |
| Pharmacogenomic Information on Dasatinib | Oncology | BCR/ABL1 | Philadelphia chromosome positive;, T315I mutation-positive | Indications and Usage, Dosage and Administration, Warnings and Precautions, Adverse Reactions, Clinical Pharmacology, Clinical Studies |
| Pharmacogenomic Information on Denileukin Diftitox | Oncology | IL2RA | CD25 antigen positive | Indications and Usage, Warnings and Precautions, Clinical Studies |
| Desipramine | Psychiatry | CYP2D6 | CYP2D6 poor metabolizers | Precautions |
| Dexlansoprazole | Gastroenterology | CYP2C19 | CYP2C19 poor metabolizers | Drug Interactions, Clinical Pharmacology |
| Dextromethorphan and Quinidine | Neurology | CYP2D6 | CYP2D6 poor metabolizers | Warnings and Precautions, Clinical Pharmacology |
| Diazepam | Psychiatry | CYP2C19 | CYP2C19 poor metabolizers | Clinical Pharmacology |
| Doxepin (1) | Psychiatry | CYP2D6 | CYP2D6 poor metabolizers | Clinical Pharmacology |
| Doxepin (2) | Psychiatry | CYP2C19 | CYP2D6 poor metabolizers | Clinical Pharmacology |
| Drospirenone and Ethinyl Estradiol | Gynecology, Dermatology | CYP2C19 | CYP2C19 intermediate metabolizers | Clinical Pharmacology |
| Eliglustat | Inborn Errors of Metabolism | CYP2D6 | CYP2D6 ultrarapid, intermediate or poor metabolizers | Indications and Usage, Dosage and Administration, Contraindications, Warnings and Precautions, Drug Interactions, Use in Specific Populations, Clinical Pharmacology, Clinical Studies |

APPENDIX-continued

| Drug | Therapeutic Area | Biomarker | Referenced Subgroup | Labeling Sections |
|---|---|---|---|---|
| Eltrombopag (1) | Hematology | F5 | Factor V Leiden carriers | Warnings and Precautions |
| Eltrombopag (2) | Hematology | SERPINC1 | Antithrombin III deficient | Warnings and Precautions |
| Erlotinib (1) | Oncology | EGFR | EGFR protein expression positive | Clinical Studies |
| Erlotinib (2) | Oncology | EGFR | EGFR exon 19 deletion or exon 21 substitution (L858R) positive | Indications and Usage Dosage and Administration, Adverse Reactions, Clinical Pharmacology Clinical Studies |
| Esomeprazole | Gastroenterology | CYP2C19 | CYP2C19 poor metabolizers | Drug Interactions, Clinical Pharmacology |
| Everolimus (1) | Oncology | ERBB2 | HER2 protein overexpression negative | Indications and Usage, Dosage and Administration, Warnings and Precautions, Adverse Reactions, Drug Interactions, Use in Specific Populations, Clinical Pharmacology, Clinical Studies |
| Everolimus (2) | Oncology | ESR1 | Estrogen receptor positive | Clinical Studies |
| Exemestane (1) | Oncology | ESR1 | Estrogen receptor positive | Indications and Usage, Dosage and Administration, Clinical Studies |
| Exemestane (2) | Oncology | PGR | Progesterone receptor positive | Clinical Studies |
| Fluorouracil (1) | Dermatology | DPYD | DPD deficient | Contraindications, Warnings, Patient Information |
| Fluorouracil (2) | Oncology | DPYD | DPD deficient | Warnings |
| Fluoxetine | Psychiatry | CYP2D6 | CYP2D6 poor metabolizers | Clinical Pharmacology, Warnings, Precautions |
| Flurbiprofen | Rheumatology | CYP2C9 | CYP2C9 poor metabolizers | Clinical Pharmacology |
| Fluvoxamine | Psychiatry | CYP2D6 | CYP2D6 poor metabolizers | Drug Interactions |
| Fulvestrant | Oncology | ESR1, PGR | Hormone receptor positive | Indications and Usage, Clinical Pharmacology, Clinical Studies |
| Galantamine | Neurology | CYP2D6 | CYP2D6 poor metabolizers | Clinical Pharmacology |
| Glimepiride | Endocrinology | G6PD | G6PD deficient | Warning and Precautions, Adverse Reactions |
| Glipizide | Endocrinology | G6PD | G6PD deficient | Precautions |
| Glyburide | Endocrinology | G6PD | G6PD deficient | Precautions |
| Pharmacogenomic Information on Ibrutinib | Oncology | del (17p) | Chromosome 17p deletion positive | Indications and Usage, Clinical Studies |
| Iloperidone | Psychiatry | CYP2D6 | CYP2D6 poor metabolizers | Dosage and Administration, Warnings and Precautions, Drug Interactions, Clinical Pharmacology |
| Imatinib (1) | Oncology | KIT | KIT protein expression positive, c-KIT D816V mutation negative | Indications and Usage, Dosage and Administration, Warnings and Precautions, Adverse Reactions, Use in Specific Populations, Clinical Pharmacology, Clinical Studies |

APPENDIX-continued

| Drug | Therapeutic Area | Biomarker | Referenced Subgroup | Labeling Sections |
|---|---|---|---|---|
| Imatinib (2) | Oncology | BCR-ABL1 | Philadelphia chromosome positive | Indications and Usage, Dosage and Administration, Warnings and Precautions, Adverse Reactions, Use in Specific Populations, Clinical Pharmacology, Clinical Studies |
| Imatinib (3) | Oncology | PDGFRB | PDGFR gene rearrangement positive | Indications and Usage, Dosage and Administration, Clincal Studies |
| Imatinib (4) | Oncology | FIP1L1-PDGFRA | FIP1L1-PDGFRα fusion kinase (or CHIC2 deletion) positive | Indications and Usage, Dosage and Administration, Clinical Studies |
| Imipramine | Psychiatry | CYP2D6 | CYP2D6 poor metabolizers | Precautions |
| Indacaterol | Pulmonary | UGT1A1 | UGT1A1-*28 allele homozygotes | Clinical Pharmacology |
| Irinotecan | Oncology | UGT1A1 | UGT1A1*28 allele carriers | Dosage and Administration, Warnings and Precautions, Clinical Pharmacology |
| Isosorbide and Hydralazine | Cardiology | NAT1-2 | Slow acetylators | Clinical Pharmacology |
| Ivacaftor | Pulmonary | CFTR | CFTR G551D, G1244E, G1349D, G178R, G551S, S1251N, S1255P, S549N, or S549R mutation carriers, F508del mutation homozygotes | Indications and Usage, Adverse Reactions, Use in Specific Populations, Clinical Pharmacology, Clinical Studies |
| Lansoprazole | Gastroenterology | CYP2C19 | CYP2C19 intermediate or poor metabolizers | Drug Interactions |
| Lapatinib (1) | Oncology | ERBB2 | HER2 protein overexpression positive | Indications and Usage, Dosage and Administration, Adverse Reactions, Use in Specific Populations, Clinical Pharmacology, Clinical Studies |
| Lapatinib (2) | Oncology | HLA-DQA1, HLA-DRB1 | HLA-DQA1*0201 or -DRB1*0701 allele carriers | Clinical Pharmacology |
| Pharmacogenomic Information on Lenalidomide | Hematology | del (5q) | Chromosome 5q deletion positive | Boxed Warning, Indications and Usage, Adverse Reactions, Use in Specific Populations, Clinical Studies |
| Letrozole | Oncology | ESR1, PGR | Hormone receptor positive | Indications and Usage, Adverse Reactions, Clinical Pharmacology, Clinical Studies |
| Lomitapide | Endocrinology | LDLR | LDLR mutation homozygotes (homozygous familial hypercholesterolemia) | Indication and Usage, Warnings and Precautions, Adverse Reactions, Clinical Studies |
| Mafenide | Infectious Diseases | G6PD | G6PD deficient | Warnings, Adverse Reactions |
| Pharmacogenomic Information on Mercaptopurine | Oncology | TPMT | TPMT intermediate or poor metabolizers | Clinical Pharmacology, Warnings, Precautions, Adverse Reactions, Dosage and Administration |
| Methylene Blue | Hematology | G6PD | G6PD deficient | Precautions |
| Metoclopramide | Gastroentrology | CYB5R1-4 | NADH cytochrome b5 reductase deficient | Precautions |
| Metoprolol | Cardiology | CYP2D6 | CYP2D6 poor metabolizers | Clinical Pharmacology |

APPENDIX-continued

| Drug | Therapeutic Area | Biomarker | Referenced Subgroup | Labeling Sections |
| --- | --- | --- | --- | --- |
| Mipomersen | Endocrinology | LDLR | LDLR mutation heterozygotes and homozygotes (heterozygous and homozygous familial hypercholesterolemia) | Boxed Warning, Indications and Usage, Warnings and Precautions, Adverse Reactions, Use in Specific Populations, Clinical Studies |
| Modafinil | Psychiatry | CYP2D6 | CYP2D6 poor metabolizers | Clinical Pharmacology, Precautions |
| Mycophenolic Acid | Transplantation | HPRT1 | HGPRT deficient | Warnings and Precautions |
| Nalidixic Acid | Infectious Diseases | G6PD | G6PD deficient | Precautions, Adverse Reactions |
| Nefazodone | Psychiatry | CYP2D6 | CYP2D6 poor metabolizers | Precautions |
| Nilotinib (1) | Oncology | BCR-ABL | Philadelphia chromosome positive | Indications and Usage, Dosage and Administration, Adverse Reactions, Use in Specififc Populations, Clinical Pharmacology, Clinical Studies |
| Nilotinib (2) | Oncology | UGT1A1 | UGT1A1*28 allele homozygotes | Clinical Pharmacology |
| Nitrofurantoin | Infectious Diseases | G6PD | G6PD deficient | Warnings, Adverse Reactions |
| Nortriptyline | Psychiatry | CYP2D6 | CYP2D6 poor metabolizers | Precautions |
| Obinutuzumab | Oncology | MS4A1 | CD20 antigen positive | Clinical Studies |
| Omacetaxine | Oncology | BCR-ABL1 | Philadelphia chromosome positive | Clinical Pharmacology, Clinical Studies |
| Omeprazole | Gastroenterology | CYP2C19 | CYP2C19 poor metabolizers | Drug Interactions |
| Panitumumab (1) | Oncology | EGFR | EGFR protein expression positive | Clinical Pharmacology, Clinical Studies |
| Panitumumab (2) | Oncology | KRAS | KRAS codon 12 and 13 mutation negative | Indications and Usage, Dosage and Administration, Warnings and Precautions, Adverse Reactions, Clinical Pharmacology, Clinical Studies |
| Pantoprazole | Gastroenterology | CYP2C19 | CYP2C19 poor metabolizers | Clinical Pharmacology |
| Paroxetine | Psychiatry | CYP2D6 | CYP2D6 extensive metabolizers | Drug Interactions |
| Pharmacogenomic Information on Pazopanib | Oncology | UGT1A1 | UGT1A1*28 allele homozygotes (TA)7/(TA)7 genotype | Clinical Pharmacology, Warnings and Precautions |
| PEG-3350, Sodium Sulfate, Sodium Chloride, Potassium Chloride, Sodium Ascorbate, and Ascorbic Acid | Gastroenterology | G6PD | G6PD deficient | Warnings and Precautions |
| Pegloticase | Rheumatology | G6PD | G6PD deficient | Contraindications, Patient Counseling Information |
| Perphenazine | Psychiatry | CYP2D6 | CYP2D6 poor metabolizers | Clinical Pharmacology, Precautions |
| Pharmacogenomic Information on Pertuzumab | Oncology | ERBB2 | HER2 protein overexpression positive | Indications and Usage, Warnings and Precautions, Adverse Reactions, Clinical Pharmacology, Clinical Studies |
| Phenytoin | Neurology | HLA-B | HLA-B*1502 allele carriers | Warnings |
| Pimozide | Psychiatry | CYP2D6 | CYP2D6 poor metabolizers | Precautions, Dosage and Administration |

APPENDIX-continued

| Drug | Therapeutic Area | Biomarker | Referenced Subgroup | Labeling Sections |
|---|---|---|---|---|
| Pharmacogenomic Information on Ponatinib | Oncology | BCR-ABL1 | Philadelphia chromosome positive; T315I mutation positive | Indications and Usage, Warnings and Precautions, Adverse Reactions, Use in Specific Populations, Clinical Pharmacology, Clinical Studies |
| Prasugrel (1) | Cardiology | CYP2C19 | CYP2C19 poor metabolizers | Use in Specific Populations, Clinical Pharmacology, Clinical Studies |
| Prasugrel (2) | Cardiology | CYP2C9 | CYP2C9 variant carriers | Use in Specific Populations, Clinical Pharmacology, Clinical Studies |
| Prasuorel (3) | Cardiology | CYP3A5 | CYP3A5 variant carriers | Use in Specific Populations, Clinical Pharmacology, Clinical Studies |
| Prasugrel (4) | Cardiology | CYP2B6 | CYP2B6 variant carriers | Use in Specific Populations, Clinical Pharmacology, Clinical Studies |
| Pravastatin | Endocrinology | LDLR | LDLR mutation heterozygotes and homozygotes (heterozygous and homozygous familial hypercholesterolemia) | Indications and Usage, Use in Specific Populations, Clinical Studies |
| Primaquine | Infectious Diseases | G6PD | G6PD deficient | Warnings and Precautions, Adverse Reactions |
| Propafenone | Cardiology | CYP2D6 | CYP2D6 poor metabolizers | Dosage and Administration, Warnings and Precautions, Clinical Pharmacology |
| Propranolol | Cardiology | CYP2D6 | CYP2D6 poor metabolizers | Clinical Pharmacology |
| Protriptyline | Psychiatry | CYP2D6 | CYP2D6 poor metabolizers | Precautions |
| Quinidine | Cardiology | CYP2D6 | CYP2D6 poor metabolizers | Precautions |
| Quinine Sulfate (1) | Infectious Diseases | G6PD | G6PD deficient | Contraindications |
| Quinine Sulfate (2) | Infectious Diseases | CYP2D6 | CYP2D6 poor metabolizers | Drug Interactions |
| Rabeprazole | Gastroenterology | CYP2C19 | CYP2C19 poor metabolizers | Drug Interactions, Clinical Pharmacology |
| Rasburicase (1) | Oncology | G6PD | G6PD deficient | Boxed Warning, Contraindications, Warnings and Precautions |
| Rasburicase (2) | Oncology | CYB5R1-4 | NADH cytochrome b5 reductase deficient | Warnings and Precautions |
| Rifampin, Isoniazid, and Pyrazinamide | Infectious Diseases | NAT1-2 | Slow acetylators (inactivators) | Clinical Pharmacology, Adverse Reactions |
| Risperidone | Psychiatry | CYP2D6 | CYP2D6 poor metabolizers | Clinical Pharmacology |
| Pharmacogenomic Information on Rituximab | Oncology | MS4A1 | CD20 antigen positive | Indications and Usage, Dosage and Administration, Adverse Reactions, Use in Specific Populations, Clinical Pharmacology, Clinical Studies |
| Simeprevir | Infectious Diseases | IFNL3 | IL28B rs12979860 T allele carriers | Clinical Pharmacology, Clinical Studies |
| Sodium Nitrite | Toxicology | G6PD | G6PD deficient | Warnings and Precautions |

APPENDIX-continued

| Drug | Therapeutic Area | Biomarker | Referenced Subgroup | Labeling Sections |
|---|---|---|---|---|
| Sodium phenylacetate and Sodium Benzoate | Inborn Errors of Metabolism | NAGS, CPS1, ASS1, OTC, ASL, ABL2 | Urea cycle enzyme deficient | Indications and Usage, Dosage and Administration, Warnings and Precautions, Adverse Reactions, Drug Interactions, Use in Specific Populations, Overdosage, Clinical Pharmacology, Clinical Studies |
| Sofosbuvir | Infectious Diseases | IFNL3 | IL28B rs12979860 T allele carriers (non-C/C genotype)IL28B | Clinical Studies |
| Succimer | Hematology | G6PD | G6PD deficient | Clinical Pharmacology |
| Sulfamethoxazole and Trimethoprim | Infectious Diseases | G6PD | G6PD deficient | Precautions |
| Tamoxifen (1) | Oncology | ESR1, PGR | Hormone receptor positive | Clinical Pharmacology, Indications and Usage, Precautions, Adverse Reactions, Medication Guide |
| Tamoxifen (2) | Oncology | F5 | Factor V Leiden carriers | Warnings |
| Tamoxifen (3) | Oncology | F2 | Prothrombin 20210A allele positive | Warnings |
| Telaprevir | Infectious Diseases | IFNL3 | IL28B rs12979860 T allele carriers (C/T and T/T genotype) | Clinical Pharmacology, Clinical Studies |
| Tetrabenazine | Neurology | CYP2D6 | CYP2D6 poor metabolizers | Dosage and Administration, Warnings and Precautions, Use in Specific Populations, Clinical Pharmacology |
| Thioguanine | Oncology | TPMT | TPMT intermediate or poor metabolizers (deficient) | Warnings, Precautions, Dosage and Administration |
| Thioridazine | Psychiatry | CYP2D6 | CYP2D6 poor metabolizers | Contraindications, Warnings, Precautions |
| Ticagrelor | Cardiology | CYP2C19 | CYP2C19 poor metabolizers | Clinical Studies |
| Tolterodine | Genitourinary | CYP2D6 | CYP2D6 poor metabolizers | Warnings and Precautions, Drug Interactions, Use in Specific Populations, Clinical Pharmacology |
| Tositumomab | Oncology | MS4A1 | CD20 antigen positive | Indications and Usage, Clinical Pharmacology |
| Tramadol | Analgesic | CYP2D6 | CYP2D6 poor metabolizers | Clinical Pharmacology |
| Pharmaeogenomic Information on Trametinib | Oncology | BRAF | BRAF V600E/K mutation positive | Indications and Usage, Dosage and Administration, Adverse Reactions, Clinical Pharmacology, Clinical Studies, Patient Counseling Information |
| Pharmacogenomic Information on Trastuzumab | Oncology | ERBB2 | HER2 protein overexpression positive | Indications and Usage, Warnings and Precautions, Clinical Pharmacology, Clinical Studies |
| Tretinoin | Oncology | PML/RARA | PML/RARα translocation positive | Clinical Pharmacology, Indications and Usage, Warnings |
| Trimipramine | Psychiatry | CYP2D6 | CYP2D6 poor metabolizers | Precautions |

APPENDIX-continued

| Drug | Therapeutic Area | Biomarker | Referenced Subgroup | Labeling Sections |
| --- | --- | --- | --- | --- |
| Valproic Acid (1) | Neurology | POLG | POLG mutation positive | Boxed Warning, Contraindications, Warnings and Precautions |
| Valproic Acid (2) | Neurology | NAGS, CPS1, ASS1, OTC, ASL, ABL2 | Urea cycle enzyme deficient | Contraindications, Warnings and Precautions |
| Pharmacogenomic Information on Vemurafenib | Oncology | BRAF | BRAF V600E mutation positive | Indications and Usage, Dosage and Administration, Warning and Precautions, Clinical Pharmacology, Clinical Studies, Patient Counseling Information |
| Venlafaxine | Psychiatry | CYP2D6 | CYP2D6 poor metabolizers | Precautions |
| Voriconazole | Infectious Diseases | CYP2C19 | CYP2C19 intermediate or poor metabolizers | Clinical Pharmacology |
| Vortioxetine | Neurology | CYP2D6 | CYP2D6 poor metabolizers | Dosage and Administration, Clinical Pharmacology |
| Warfarin (1) | Cardiology or Hematology | CYP2C9 | CYP2C9 intermediate or poor metabolizers | Dosage and Administration, Drug Interactions, Clinical Pharmacology |
| Warfarin (2) | Cardiology or Hematology | VKORC1 | VKORC1 A allele carriers | Dosage and Administration, Clinical Pharmacology |
| Warfarin (3) | Cardiology, Hematology | PROS | Protein S deficient | Warnings and Precautions |
| Warfarin (4) | Cardiology, Hematology | PROC | Protein C deficient | Warnings and Precautions |

What is claimed is:

1. A system to provide information on a drug substance for a subject, comprising:
   a processor computer at a production point to match genomic biomarker(s) from gene or DNA sequencing for a population with historical information for a population on drug structure, dosage, clinical variability and risk for adverse events for the drug substance, the computer constructing gene-drug-drug interactions (GDDIs) training dataset with pharmaceutical, pharmacokinetic (PK), pharmacogenetic (PG), and pharmacodynamic (PD) GDDIs from multiple data sources for each drug in a set of drugs under consideration, the computer constructing side effect features for each of the drugs in the set from genetic panels for an individual and side effects associated with the drugs in the set using the GDDIs training dataset, and a GDDIs classifier to predict whether a drug pair derived from the set of drugs results in adverse interactions, the computer generating one or more indicia as a container label of the drug substance with:
   genotype-specific dosing based on the gene or DNA;
   polymorphic drug target and disposition genes;
   treatment based on the genomic biomarker; and
   a printer and a scanner connected to another computer to print by receiving the one or more indicia and applying the one or more genomic biomarkers to the indicia to select a custom dosage and based on the selected custom dosage by performing the custom pharmacy compounding or custom production of a drug whose properties are selected and crafted for the individual patient to provide personalized medicine.

2. The system of claim 1, wherein the biomarkers comprise at least one of: germ-line or somatic gene variants, functional deficiencies, expression changes, chromosomal abnormalities, and protein biomarkers used to select patients for treatment.

3. The system of claim 1, comprising indicia on gene, protein or chromosomal testing, genetic testing, functional protein assays, cytogenetic studies before using the drug and an indicia about changes in efficacy, dosage or toxicity due to genetic variants, an indicia on a gene or protein involved in the metabolism or pharmacodynamics of the drug, and an indicia that the gene or protein leads to different response.

4. The system of claim 1, comprising a code communicating with: a gene-drug interactions training dataset that includes pharmaceutical and pharmacogenomics interactions for the drug; a side effect feature database for the drug from gene sensitivity associated with the drug; a gene-drug interactions classifier that predicts adverse gene-drug interactions for drug gene pairs and a subject's genetic scan; and for each of the side effects, a Fisher's exact test to determine predicted gene-drug-drug interactions.

5. The system of claim 1, wherein the substance is a drug, comprising code for: constructing a gene-drug interactions training dataset that includes pharmaceutical, pharmacokinetic or pharmacodynamics, and pharmacogenomics drug-drug interactions for each drug; constructing side effect features for each of the plurality of drugs from side effects associated with the plurality of drugs; running a gene-drug-drug interactions classifier that predicts adverse drug-drug interactions for drug pairs and the genetic scan; and for each of the side effects, performing a Fisher's exact test to determine predicted gene-drug-drug interactions.

6. The system of claim 5, wherein the gene-drug-drug interactions classifier uses a classifying objective function having a smoothness constraint and a fitting constraint to render the predicted adverse gene-drug interactions.

7. The system of claim 1, comprising code for building a genetic drug-drug interactions classifier using deep learning with a neural network, comprising propagating drug-drug interactions between different ones of the plurality of drugs on a basis that if a first drug has an interaction with a second drug and the second drug is similar to a third drug, then the first drug is considered as having interaction with the third drug.

8. The system of claim 1, wherein the indicia comprise a bar code, a near field communication (NFC) transmission, a text, or an Internet link.

9. The system of claim 1, wherein the indicia is readable by a smart phone, comprising code to update the indicia with changes in the subject after the consumption of the substance.

10. The system of claim 1, comprising a gene sequencer to capture genetic data from the subject, wherein the indicia is updated with changes in the subject after the consumption of the substance.

11. The system of claim 1, comprising a module detect the evolutionary paths of escape.

12. The system of claim 1, comprising a hidden markov model (HMM) to detect evolutionary paths of escape.

13. The system of claim 1, comprising a module to detect mutation by comparing later sequence reads by a genetic analyzer with prior sequence reads.

14. The system of claim 1, comprising a module to detect an amount of mutation cancer polynucleotides in a sample from a subject over time by determining a frequency of the cancer polynucleotides at a plurality of time points; determining an error range for the frequency at each of the plurality of time points; determining, between an earlier and later time point, whether error ranges (1) overlap, indicating stability of frequency, (2) an increase at the later time point outside the error range, indicating increase in frequency or (3) a decrease at the later time point outside the error range, indicating decrease in frequency.

15. The system of claim 1, comprising a model to infer tumor phylogeny from sequencing data, wherein subclones are related to each other by an evolutionary process of acquisition of mutations.

16. The system of claim 1, comprising a deep learning machine using deep convolutional neural networks for detecting genetic based drug-drug interaction.

17. The system of claim 1, comprising drug interaction database.

18. The system of claim 1, comprising a module for analyzing a disease state of a subject by collecting genetic profile data on a population of tumors and original tumor treatment(s); identifying one or more evolutionary paths of escape and evolved tumor treatment(s); and based on a subject profile, predicting a probability of escape along the one or more evolutionary paths.

19. The system of claim 1, comprising a module to recommend drug repurposing using drug-effect similarities from existing therapeutic indications of known drugs.

20. The system of claim 1, comprising a module to predict side effects before a drug enters a clinical trial.

* * * * *